US012806339B2

(12) United States Patent
Hassani

(10) Patent No.: US 12,806,339 B2
(45) Date of Patent: Nov. 24, 2026

(54) INTRAVENOUS FLUID DELIVERY SYSTEM AND APPARATUS

(71) Applicant: DASH Anesthesia, Chicago, IL (US)

(72) Inventor: Dane Hassani, Chicago, IL (US)

(73) Assignee: DASH Anesthia, Chicago, IL (US)

( * ) Notice: Subject to any disclaimer, the term of this patent is extended or adjusted under 35 U.S.C. 154(b) by 141 days.

(21) Appl. No.: 18/480,854

(22) Filed: Oct. 4, 2023

(65) Prior Publication Data

US 2024/0024574 A1 Jan. 25, 2024

Related U.S. Application Data

(62) Division of application No. 17/335,996, filed on Jun. 1, 2021, now Pat. No. 11,806,506.

(60) Provisional application No. 63/032,857, filed on Jun. 1, 2020.

(51) Int. Cl.

| | |
|---|---|
| ***A61M 5/168*** | (2006.01) |
| ***A61J 1/14*** | (2023.01) |
| ***A61M 39/24*** | (2006.01) |
| *A61J 1/05* | (2006.01) |

(52) U.S. Cl.
CPC ........ *A61M 5/16827* (2013.01); *A61J 1/1437* (2013.01); *A61M 39/24* (2013.01); *A61J 1/05* (2013.01); *A61J 2205/10* (2013.01); *A61J 2205/40* (2013.01); *A61J 2205/60* (2013.01); *A61M 2205/502* (2013.01); *A61M 2205/6045* (2013.01)

(58) Field of Classification Search
CPC .............. A61M 5/16827; A61M 39/24; A61M 2205/502; A61M 2205/6045; A61J 1/1437; A61J 1/05; A61J 2205/10; A61J 2205/40; A61J 2205/60; E05B 39/02; E05B 39/00; E05B 39/025; G09F 3/0317; G09F 3/0358; Y10T 292/31; Y10T 292/48; Y10T 292/51; Y10T 70/5031
See application file for complete search history.

(56) References Cited

U.S. PATENT DOCUMENTS 7,064,032 B2 * 6/2006 Hsu ........................ H10B 43/30
438/257
9,744,290 B2 * 8/2017 Tieck .................... A61M 39/10
2002/0014962 A1 * 2/2002 Miglioli ................. G08B 13/22
340/568.1
2022/0063883 A1 * 3/2022 Mott ..................... A61J 1/1412

FOREIGN PATENT DOCUMENTS

CN 103476486 A * 12/2013 .......... A61M 1/3672

* cited by examiner

*Primary Examiner* — Brian A Zimmerman
*Assistant Examiner* — Anthony D Afrifa-Kyei
(74) *Attorney, Agent, or Firm* — Flener IP & Business Law

(57) ABSTRACT

An intravenous fluid delivery apparatus (IFDA) includes a body having two or more docks, wherein each dock includes a dock outlet and is configured to engage with a container. The IFDA further includes a fluid interface having two or more interface inlets and an interface outlet, wherein the two or more interface inlets are in fluid communication with the interface outlet, and two or more supply lines, each supply line disposed between one of the dock outlets and one of the interface inlets, wherein the interface outlet is configured to connect with an intravenous line.

12 Claims, 4 Drawing Sheets

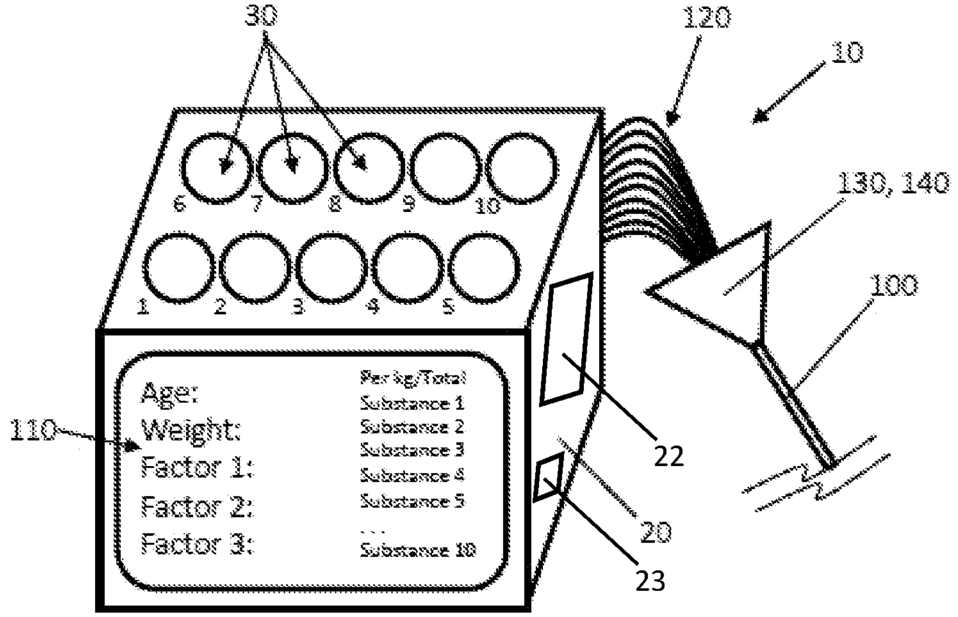
Figure 1
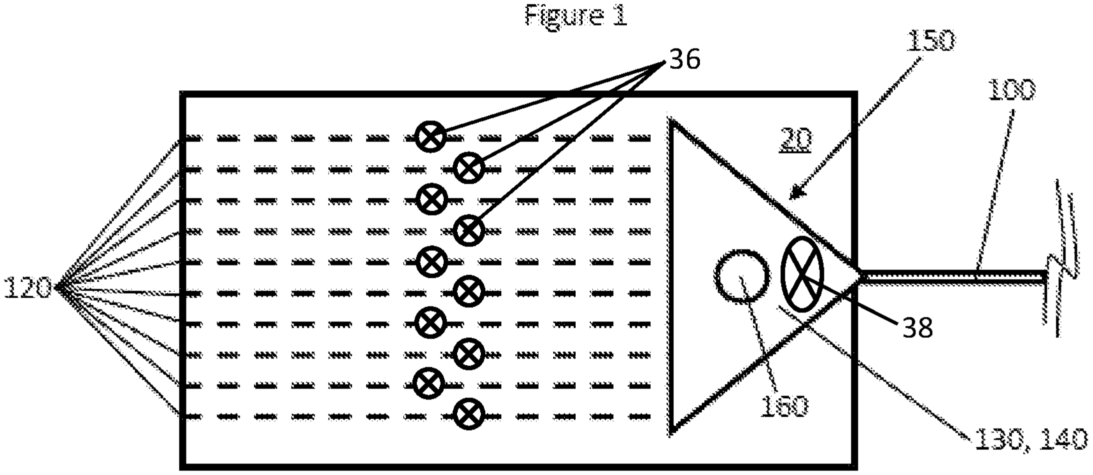
Figure 1A
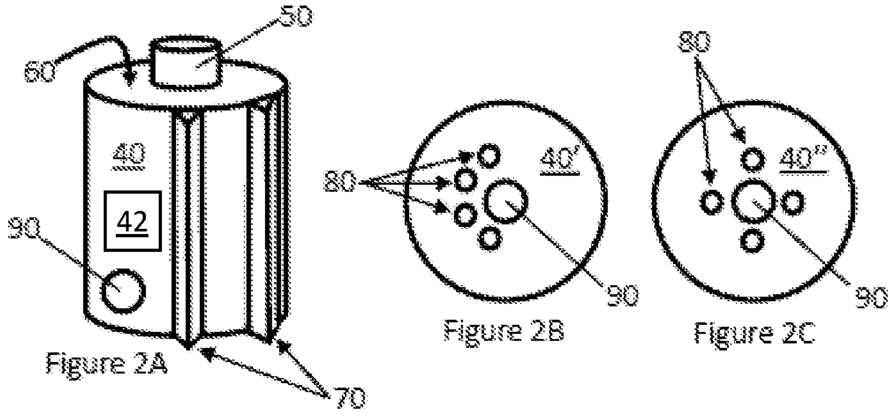
Figure 2A
Figure 2B
Figure 2C

Docks Status

Dock 1: Locked - Enter Passcode to Unlock
Dock 2: Locked - Enter Passcode to Unlock
Dock 3: Chamber Empty – Unlock to Remove
Dock 4: Dock Empty – Insert Chamber or Assign Passcode
Dock 5: Locked - Enter Passcode to Unlock
Dock 6: Locked - Enter Passcode to Unlock
Dock 7: Locked - Enter Passcode to Unlock 110
Dock 8: Locked - Enter Passcode to Unlock
Dock 9: Locked - Enter Passcode to Unlock
Dock 10: Locked - Enter Passcode to Unlock

Figure 3

Controlled Substance Usage Status

Substance 1: 2.648 kg
Substance 2 : 1.453 kg
Substance 3: 0 kg
Substance 4: 0 kg
Substance 5: 2.908 kg
Substance 6: 0 kg
Substance 7: 3.872 kg
Substance 8: 0 kg 110
Substance 9: 9.778 kg
Substance 10: 0 kg

Figure 4

INTRAVENOUS FLUID DELIVERY SYSTEM AND APPARATUS

CROSS-REFERENCE TO RELATED APPLICATIONS

This application is a divisional of U.S. patent application Ser. No. 17/335,996 filed on Jun. 1, 2021, which claims the benefit of priority to U.S. Provisional Patent Application No. 63/032,857 filed on Jun. 1, 2020, and incorporated in its entirety by reference herein.

FIELD OF THE INVENTION

The present invention relates to an intravenous fluid delivery system. More specifically, the present invention relates to an intravenous fluid delivery system including a plurality of replaceable fluid chambers and a user interface for controlling delivery of the fluids.

BACKGROUND OF THE INVENTION

Fluid delivery systems are known in the art. However, known systems are typically for delivery of a breathable anesthetic and do not allow for intravenous delivery. For example, Rumph, et al., U.S. Pat. No. 7,836,882 discloses an electronic anesthesia delivery system having a chassis that accommodates first and second anesthetic chambers and an oxygen input port. A touchscreen graphic display controls the oxygen input port and at least one valve in fluid communication with each of the first and second anesthetic chambers to control a flow rate and concentration of delivered anesthesia.

While infusion pumps are ubiquitous in healthcare, the only device commonly used to deliver a bolus dose of a drug is known as a Patient Controlled Analgesia (PCA). PCAs typically use a syringe pump, which requires a plunger at the end of a full syringe, thus adding substantial length to the device. Therefore a need exists for a device that can administer a bolus dose of a fluid, for example without limitation, a controlled or non-controlled substance, from a more compact medication container than previous devices, for example, a device that utilizes a roller mechanism as disclosed herein.

With the exception of volatile agents and continuous infusions, all medications are currently manually removed from a medication cart and administered via syringe into the patient's IV line. There are no known systems for controlled delivery of two or more fluids, for example without limitation, two or more controlled substances such as fentanyl, ketamine, morphine, hydromorphine, and the like, to an intravenous line. Therefore, a need exists for an intravenous fluid delivery system or apparatus that provides for a secure containment and controlled delivery of a mix of two or more fluids, for example without limitation the controlled substances listed above, to an intravenous line. It would be beneficial if a unidirectional bacteriostatic valve is incorporated into a disposable cartridge forming an interface between delivery lines from the chambers and the intravenous line.

It is unique to the practice of anesthesia to have the provider simultaneously prescribe, dispense, and administer a medication. Normally these tasks are split among a physician, pharmacist, and nurse. In the high acuity environment of the operating room, medication errors can occur due to a number of reasons including mislabeling syringes or selecting the wrong vial. It would therefore be beneficial if the fluid delivery system or apparatus was able to eliminate the potential for error due to the self-contained nature of the medications. It would be further beneficial to have a user interface allowing for a delivery mixture of the two or more fluids on either a per-kilogram patient weight amount or a total amount of each fluid to be delivered, while further allowing for better reconciliation of the fluids.

Anesthesia providers are among the highest risk groups for drug diversion and abuse. Despite all current efforts, diversion is still possible due to easy access to vials of medications. Therefore, a need exists for a device that can help decrease provider diversion, for example, via the secure containment of fluids, for example without limitation, controlled substances, and direct injection into a patient's IV line. It would be beneficial if the fluid delivery system or apparatus includes replaceable fluid chambers or disposable bottles. It would be further beneficial if the replaceable chambers or disposable bottles could lock into place within receivers or docks in the apparatus wherein the replaceable chambers or disposable bottles could only be removed with the entry of a passcode or passkey. Each of the individual replaceable fluid chambers or disposable bottles could also be keyed or otherwise include a pattern of pins allowing the chamber to fit only into the corresponding receiver or dock for which it is designed. The current invention is believed to be the first device to incorporate the storage, administration, and reconciliation of anesthetic medications.

SUMMARY OF THE INVENTION

In one aspect of the invention, an intravenous fluid delivery apparatus (IFDA) comprises a body having two or more docks, wherein each dock includes a dock outlet and is configured to engage with a container. The IFDA further comprises a fluid interface having two or more interface inlets and an interface outlet, wherein the two or more interface inlets are in fluid communication with the interface outlet, and two or more supply lines, each supply line disposed between one of the dock outlets and one of the interface inlets, wherein the interface outlet is configured to connect with an intravenous line.

In another aspect of the invention, an intravenous fluid delivery apparatus (IFDA) comprises a body having two or more openings, wherein each opening is configured to engage with a container that includes a container outlet. The IFDA further comprises a fluid interface having two or more interface inlets and an interface outlet, wherein the two or more interface inlets are in fluid communication with the interface outlet, and two or more supply paths, each supply path comprising a replaceable distribution element and a connecting tube disposed between one of the container outlets and one of the interface inlets, wherein the interface outlet is configured to connect with an intravenous line In a further aspect of the invention, a container configured for use with an intravenous fluid delivery apparatus comprises a valve or opening disposed on the container, an electronic tag circuit disposed on the container, a non-permanent data storage memory disposed on the electronic tag circuit, and an identifying element stored in the non-permanent data storage memory.

BRIEF DESCRIPTION OF THE DRAWINGS

FIG. 1 is a schematic view of an exemplary first embodiment of an intravenous fluid delivery apparatus;

FIG. 1A is a schematic view of an exemplary second embodiment of the supply lines and disposable interface cartridge of an intravenous fluid delivery apparatus;

FIG. 2A is an exemplary first embodiment of a chamber for a fluid as used in the intravenous fluid delivery apparatus;

FIG. 2B is an exemplary second embodiment of a chamber for a fluid as used in the intravenous fluid delivery apparatus;

FIG. 2C is an exemplary third embodiment of a chamber for a fluid as used in the intravenous fluid delivery apparatus;

FIG. 3 is a schematic view of an exemplary screen shot for a dock status screen of a user interface of an intravenous controlled delivery apparatus;

FIG. 4 is a schematic view an exemplary screen shot for a substance usage screen of a user interface of an intravenous controlled delivery apparatus;

Other aspects and advantages of the present invention will become apparent upon consideration of the following detailed description, wherein similar structures have similar reference numerals.

DETAILED DESCRIPTION

Figure 2D:
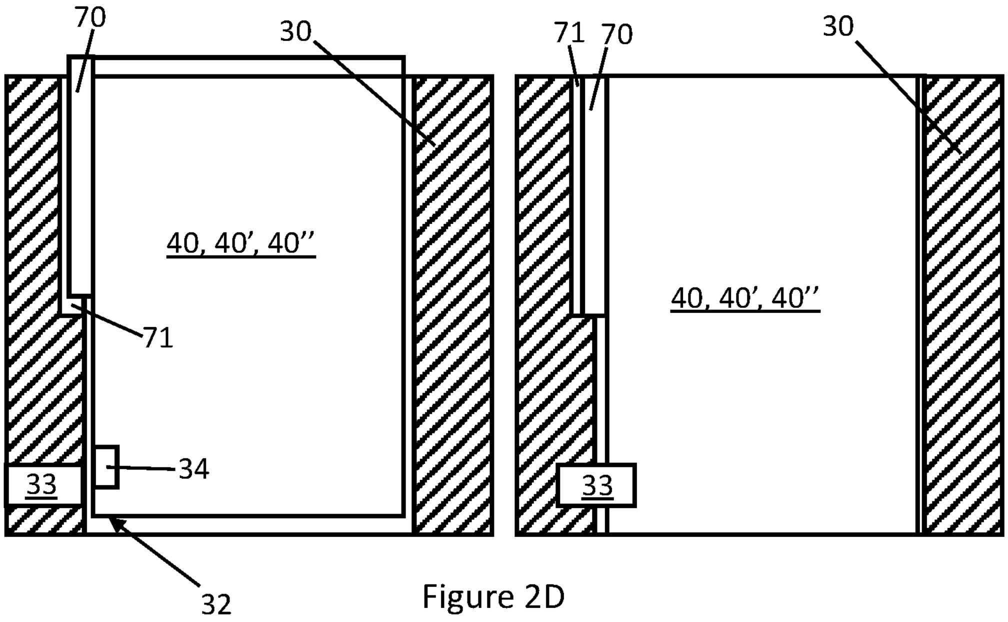
FIG. 2D is an exemplary cross-sectional view of a dock showing features of an embodiment of a locking mechanism and an embodiment of identifying elements as used in the intravenous fluid delivery apparatus.

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Referring to FIG. 1, an embodiment of an intravenous fluid delivery apparatus (IFDA) 10 is illustrated with a housing or body 20 having 10 openings or docks 30, each configured to accommodate and/or engage with a replaceable container or chamber 40, 40', 40" each containing a specific fluid. The body 20 also includes a clamp (not shown) as is well known in the art such that the body 20 can be secured onto an intravenous (IV) pole.

FIG. 1 illustrates there to be 10 docks 30; however, the actual number may be for example, without limitation, any number between 2 and an upper limit that is limited only by the physical space available within the body 20. For example, in one embodiment the total number of docks 30 is 50, while in another embodiment the number of docks 30 is 25, and in yet another embodiment the number of docks 30 is 5. In addition, though the docks 30 are shown in the schematic view of FIG. 1 to be circular, they may in fact have any cross-sectional shape and may further include patterned grooves or recesses as may be known in the art or as otherwise desirable and as further described hereinbelow in relation to the chambers 40, 40', 40". The docks 30 may additionally include a cover (not shown), for example a hinged or sliding door, to keep debris or other contaminants out of the docks 30.

Referring to FIG. 2A-2C, non-limiting exemplary embodiments of a chamber 40, 40', 40" are illustrated each having a set of identifying elements that is unique to a fluid contained therein and that are complementary to a set of identifying elements disposed within one or more of the docks 30. In FIG. 2A, a first exemplary embodiment of the chamber 40 is shown in side perspective having a small handle 50 at a top end 60 thereof. The exemplary embodiment of the chamber 40 includes a first set of identifying elements comprising one or more radial splines 70 (see FIG. 2D) that are positioned on the chamber 40 based on the type of fluid stored within the chamber 40. A first particular dock 30 on the body 20 meant to accommodate the fluid within the chamber 40 has a second set of identifying elements that are complementary to the first set of identifying elements, for example, grooves 71 (see FIG. 2D) to allow the chamber 40 to be inserted into it. In this way, only chambers 40 having the particular fluid meant for use with the first particular dock 30 are physically capable of being inserted into and engaging with the first particular dock 30.

In other embodiments, for example without limitation, the chamber 40' in FIG. 2B or the chamber 40" in FIG. 2C, instead of or in addition to the splines 70, the chamber 40' or 40" has other sets of identifying elements comprising, for example, two or more pins 80 that extend outwardly in a pattern from a bottom surface thereof. The two or more pins 80 are patterned on the chamber 40' or 40" based on the type of fluid stored within the chamber 40' or the chamber 40". A second or third particular dock 30 on the body 20 meant to accommodate the fluid within the chamber 40' or 40" has complementary sets of identifying elements, for example, recesses (not shown) matching the pattern of the pins 80 to allow the chamber 40' or 40" to be inserted into it. In this way, only chambers 40' or 40" having the particular fluid meant for use with the second or third particular dock 30 are physically capable of being inserted into and engaging with the second or third particular dock 30.

The docks 30 and the chambers 40, 40', 40" may have other matching structures, keys, pins, splines, patterns, cross-sectional shapes, combinations of any of the foregoing, or any suitable mechanism as may be known in the art to ensure that only the chamber 40, 40', 40" containing the fluid meant for a particular dock 30 can be secured within that particular dock 30. In addition, as noted hereinbelow, other embodiments of containers 240 include electronic tags or other non-structural identifying elements indicative of the contents thereof, wherein the electronic tags or other non-structural identifying elements are intended to match with the same electronic tags or other non-structural identifying elements associated with each dock 230.

Such a mechanism for matching a particular fluid to a particular dock 30 by allowing only the corresponding chamber 40, 40', 40" to be inserted into that particular dock provides that the same fluid is always passed through a particular dock 30. Returning to FIG. 1, in one embodiment, the body 20 includes 5 docks 30 that accommodate and/or engage with 5 replaceable chambers 40, 40', 40" containing, for example without limitation, commonly used medications such as propofol, fentanyl, rocuronium, lidocaine, and succinylcholine.

The chambers 40, 40', and 40" in some embodiments further include electrical contacts on an outer surface thereof that line up with and engage electrical contacts on an inside of the corresponding dock 30 when the chamber 40, 40', 40" is inserted therein. Engagement of the electrical contacts provides electrical communication between circuitry 22 (see FIGS. 1 and 5) disposed in or on the body 20 (or 220) that, for example without limitation, executes control logic for the control of delivery of the fluids and electronic components or other circuitry that may be disposed on the chamber 40, 40', 40". The circuitry 22 in or on the body 20 may be in the form of a processing unit including input and output channels, and volatile and permanent memory storage space as may be known in the art for the control of multiple valves and flow measurement devices and/or the collection of data associated therewith.

As visible in FIGS. 2A, 2B, and 2C, each of the embodiments of the chamber 40, 40', and 40", respectively, includes a valve 90. In some embodiments, the valve 90 is disposed on a bottom surface of the chamber 40', 40" as illustrated in FIGS. 2B and 2C, whereas in other embodiments the valve 90 is disposed on a side surface of the chamber 40 as illustrated in FIG. 2A. The valve 90 is described more fully in connection with operation of the apparatus 10 hereinbelow.

Returning to FIG. 1, the IFDA 10 is an enclosed system that directly delivers fluids, for example without limitation, medications or other controlled substances such as fentanyl, ketamine, morphine, hydromorphine, and the like to an intravenous (IV) line 100. To further the following discussion the docks 30 in FIG. 1 have been provided exemplary numbers 1 through 10. The substance within a chamber 40, 40', 40" having been inserted into dock 30 number 1 may be referred to in shorthand as substance 1. Similarly, the substance within a chamber 40, 40', 40" having been inserted into dock 30 number 2 may be referred to in shorthand as substance 2, and so on.

Once the chambers 40, 40', 40" are secured in their corresponding docks 30, the apparatus 10 is ready for use. In one embodiment, a side of the apparatus 10 includes a user interface 110 that communicates with the circuitry 22 within or on the body 20. In another embodiment, the user interface 110 may be on a separate electronic device (not shown) that communicates with the circuitry 22 within or on the body 20, for example on a laptop, desktop, or tablet computer, a smart phone device running an application for the user interface 110 or any other suitable electronic platform that can generate an interactive user interface as may be known in the art. In one embodiment a user may enter patient age and weight into the user interface 110, and then be able to choose a delivery regime wherein the amount of each of the fluids in the chambers 40, 40', 40" can be specified either on a per-kilo of patient weight basis or as a total amount of each drug to be delivered basis. For example, a user may specify 0.02 grams of substance 1 per patient kg, 0.05 kg of substance 2 per patient kg, 0.008 grams of substance 3 per patient kg, etc . . . Alternatively, the user may specify a total amount of substance 1, a total amount of substance 2, a total amount of substance 3, etc. Upon entry of the specified amounts of each of the fluids to be delivered, the apparatus 10 via the circuitry 22 in or on the body 20 computes the rates of delivery for each of the fluids.

In one embodiment the user interface 110 switches between input modes for age, weight, and delivery regimes by a simple touch on a particular portion of the user interface 110 screen. In other embodiments the user interface 110 switches between input modes for age, weight, and delivery regimes by any other suitable method as is known in the art, for example by being connected with a keyboard and accepting input via the keyboard.

In an embodiment, in addition to inputting the age and weight of the patient, the user may further input additional factors that may be used to specify how much of each of the fluids is to be delivered. For example, the additional factors can include patient allergies to medications, patient health issues, or other factors of importance to how much and what fluids can safely be delivered to the patient. In other embodiments, the additional factors may be used for other purposes, for example, the additional factors are recorded and kept as a record of the other factors values for later analysis. In one embodiment the circuitry 22 in or on the body 20 includes or is electrically connected with a permanent or non-volatile data storage device 23 (see FIG. 1) for example, a disk drive, flash drive, solid state drive, or other type of permanent memory as is known in the art for recording of the data of the additional factors as well as other data as will be further described hereinbelow.

Once the delivery regime has been established and the amounts for each of the fluids has been input via the user interface 110, delivery of the pre-specified mixture of the fluids may begin. In one embodiment, delivery begins when a user enters a start command via the user interface 110, for example, by touching a virtual start button or other virtual graphic (not shown) that triggers the delivery to begin. In other embodiments, delivery may be started and/or stopped via a user input on a remote device communicating with the circuitry 22 in or on the body 20 connected to the apparatus 10 by wires or wirelessly as is known in the art. Regardless of the mechanism for triggering the start of delivery, upon receiving the trigger, the circuitry 22 disposed within or on the body 20 executes the required control logic to begin the delivery process.

On a physical fluid level, delivery requires that the fluids within the pre-selected chambers 40, 40', 40" be allowed to flow out therefrom. To that end the valve 90 on each of the chambers 40, 40', 40" mates with a connection or receiving valve within its matching dock 30. A seal around the connection prevents leakage of any of the fluid when the valve 90 is opened, so that upon opening of the valve 90 any fluid that flows out of the chamber 40, 40', 40" flows only into a supply line associated with the particular dock 30 associated with the chamber 40, 40', 40". In one embodiment, the valve 90 on each of the chambers 40, 40', 40" is electronically opened by the control logic. In another embodiment, the valve 90 on each of the chambers 40, 40', 40" has no electronic component and is mechanically opened upon placement of the chamber 40, 40', 40" into its associated particular dock 30. A metering valve 36 (see FIG. 1A) or other like device as is known in the art is disposed in the supply line associated with each dock 30. In one embodiment, each metering valve 36 is controlled by the control logic to allow a predetermined rate of the fluid to pass through it.

Referring again to FIG. 1, a plurality of supply lines 120 is shown schematically exiting from the body 20. Each of the supply lines 120 is connected at an upstream end with one of the docks 30. Fluids from each of the docks 30 being utilized flows through a metering valve 36 or the like at a prescribed rate into each of the supply lines 120. All of the supply lines 120 come together at a fluid interface 130 that fluidly connects the plurality of supply lines 120 on an input side of the fluid interface 130 to an intravenous (IV) line 100 on an output side of the fluid interface 130. The fluid interface 130 includes a unidirectional bacteriostatic valve 38 (see FIG. 1A) for connection to the IV line 100. Such a valve is crucial to assure there is no cross contamination between the patient and any of the supply lines 120. In one embodiment, the fluid interface 130 including the unidirectional bacteriostatic valve 38 is incorporated into a disposable cartridge 140 that can be replaced after each use.

In another embodiment, the supply lines are internal to the body 20. Referring to FIG. 1A, in this embodiment the supply lines 120 shown as dashed lines are embedded in the body 20. As with prior embodiments, each of the supply lines 120 includes a metering valve 36 or the like as may be known in the art for controlling a prescribed rate of flow of a fluid through the line. In this embodiment the fluid interface 130 comprising the disposable cartridge 140 snaps into and out of a recess 150 in the body 20. In one embodiment the cartridge 150 includes a handle 160 to assist in snapping the cartridge 140 into and out of the recess 150.

In an embodiment, once a chamber 40, 40', 40" is secured within a corresponding dock 30 as explained hereinabove, a locking mechanism 32 within the dock 30 is electronically actuated to prevent removal of the chamber 40, 40', 40". For example, the circuitry 22 within or on the body and the user interface 110 operate to control the locking mechanism 32 disposed within each dock 30, wherein the locking mechanism 32 is configured to prevent removal of the chamber 40, 40', 40" once the chamber 40, 40', 40" is engaged in the dock 30, and wherein the circuitry 22 within or on the body is configured to release the locking mechanism 32 to allow removal of the chamber 40, 40', 40".

In an embodiment, upon completion of delivery of the predetermined amounts of the fluids, the chambers 40, 40', 40" cannot be removed from their docks without entry of a key or passcode into the user interface 110. Referring to FIG. 3, in one embodiment the user interface 110 displays a status view for all of the docks 30 in the body 20. Each chamber 40, 40', 40" cannot be removed unless a correct passcode is entered. In one embodiment the passcode is entered via the user interface 110, for example by touching the text indicating "Enter Passcode." Entry of a correct passcode entered into the use interface 110 is communicated to circuitry 22 within or on the body 20, which subsequently controls release of the locking mechanism 32, which may for example without limitation be any sort of electronically controlled latch, hook, pin or other structure 33 that extends from a side wall of the dock 30 and engages with a complementary structure or recess 34 on the chamber 40, 40', 40" to prevent extraction of the chamber 40, 40', 40" from the dock 30. For example, referring to FIG. 2D, a dock 30 is shown on the left with a chamber 40, 40', 40" inserted therein and a locking mechanism 32 not yet actuated, and on the right with the pin 33 extended into the complementary structure or recess 34.

The passcode may be established for each of the chambers 40, 40', 40" by any method as may be known in the art. For example, without limitation, in one embodiment the passcode for each chamber 40, 40', 40" is established upon insertion of the chamber 40, 40', 40" into its dock 30. In this embodiment, for example as illustrated in FIG. 3, a passcode is assigned before insertion by touching the user interface 110, for example, where it says, "Assign Passcode." After entering a suitable passcode of predetermined length and/or complexity, the user interface 110 would prompt the user to physically insert the chamber 40, 40', 40" into its dock 30, and upon insertion of the chamber 40, 40', 40" the passcode is electronically coded onto the chamber 40, 40', 40" for subsequent reading by the circuitry 22 in or on the body 20. The electronic coding disposed onto the chamber 40, 40', 40" can be by any sort of optical or electronic barcode, VR code, RFID tag, or other type of electronic coding as is known in the art disposed on or as part of any corresponding electronic tag circuit, for example, one or more integrated circuits (ICs), a circuit board having discrete components, a combination of a circuit board having discrete components and one or more ICs, or any other suitable electronic tag circuit as is known in the art and as represented by element 42 in FIG. 2A.

In another embodiment, the passcode for each chamber 40, 40', 40" is predetermined and is a part of the chamber itself. For example, each chamber 40, 40', 40" may have an electronically coded passcode that is read by the circuitry 22 in or on the body 20 upon insertion of the chamber 40, 40', 40" into its dock 30. The electronically coded passcode would therefore be established without entry of the passcode by a user. In a further embodiment unopened and unused chambers 40, 40', 40" could have an initial passcode indicative of being new and unused and could require the entry of a subsequent passcode by a user upon first insertion into the dock 30 of the IFDA 10.

In an embodiment, the passcode that is electronically encoded on each chamber 40, 40', 40" is stored in a non-permanent memory, for example a random-access memory (RAM), a re-writeable flash drive, or other non-permanent memory as is known in the art disposed on or as part of an electronic tag circuit 42 disposed on the chamber 40, 40', 40". The non-permanent memory provides a tamper resistant mechanism for the chamber 40, 40', 40". For example, in this embodiment the passcode is erased from the non-permanent memory if the chamber 40, 40', 40" is in any way opened or otherwise tampered with to gain access to the fluid within.

For example, in this embodiment, a breakable electric circuit is disposed on the chamber 40, 40', 40" wherein the circuit is completed by the electronic tag circuit 42 connected through a cap, a cover over an opening, or a valve 90 on the chamber 40, 40', 40". The electronic tag circuit 42 is connected with a capacitor or a storage cell or any power storage element as is known in the art that is disposed in or on the chamber 40, 40', 40". In the absence of any tampering the integrity of the cap, cover, or valve 90 remains intact and the circuit remains unbroken. However, if someone with the goal of diverting the fluid from within the chamber 40, 40', 40" by for example trying to unscrew the cap or remove the cover over the opening or open the valve 90 thereon, such action disturbs the electrical connection between the electronic tag circuit 42 and the cap, the cover, or the valve 90, for example, by breaking the electric circuit. Such disturbance causes the electronic tag circuit 42 to erase the non-permanent memory, by either removing power from the non-permanent memory or by overwriting the data in the non-permanent memory with a null field, thereby eliminating the passcode. A chamber 40, 40', 40" thus tampered with will be rejected for use by the IFDA as lacking a passcode.

In another embodiment, the circuitry 22 in or on the body 20 would also be capable of determining when a chamber 40, 40', 40" had become empty, for example through the use of flow meters in each of the supply lines, a pressure sensor associated with each supply line, a measurement of the weight of each chamber with knowledge of the empty weight thereof, a computation of the known and previously stored starting volume data for the chamber 40, 40', 40" minus the volume of fluid passed through a flow meter, or any other mechanism for determining that a chamber 40, 40', 40" had emptied as may be known in the art. Upon determining that a chamber 40, 40', 40" had become empty, in one embodiment the user interface 110 prompts the user to remove the chamber 40, 40', 40" from its dock 30. Referring again to FIG. 3, prior to removal the user interface 110 requires that the chamber 40, 40', 40" first be unlocked—as illustrated by the exemplary text "Chamber Empty—Unlock to Remove." Upon a user touching the indicated text, the user interface 110 would prompt for the required passcode.

A benefit of utilizing chambers 40, 40', 40" for specific fluids only in connection with particular matching docks 30 is that the amounts used for each of the fluids can be closely tracked, and a record kept. Referring to FIG. 4, for example without limitation, the user interface 110 includes a Usage Status screen that indicates a log of the amount of each of the fluids delivered by the apparatus 10. This log could be reset or have multiple versions each initiated at different points in time. Units used for the amount of each fluid could be in weight or by liquid volume as preferred by the physicians using the apparatus 10 or as may be otherwise known in the art. The user interface 110 could store the usage data in the logs to a permanent electronic storage device, for example a disk drive, a flash drive, a solid-state drive, or other form of electronic data storage 23 as is known in the art, where the permanent electronic data storage 23 device may be internal to the body 20 or external to the body 20 and accessible via a port in the body or a networked connection from the circuitry 22 within or on the body 20.

Utilizing the ability of the circuitry 22 in or on the body 20 to determine the weight of a chamber 40, 40', 40", the IFDA 10 can also prevent the use of chambers 40, 40', 40" that have had a portion of the contents removed without prior authorization or record. As further described above, usage data for each chamber 40, 40", 40" is stored in a log so that the volume of every chamber 40, 40', 40" is always known and the contents of all of the chambers 40, 40', 40" is accounted for. In an embodiment, the IFDA 10 detects the weight and therefore the volume of fluid within a chamber 40, 40', 40" and compares that volume to the expected known volume of the chamber 40, 40', 40" as stored in the log. If there's a discrepancy between the measured volume and the expected known volume of the chamber 40, 40', 40" a possible reason could be that a portion of the volume of the chamber 40, 40', 40" has been withdrawn without a proper authorization or accounting thereof. If such is the case, in an embodiment the IFDA 10 detects the discrepancy and rejects any further use of the chamber 40, 40', 40" until such time as an administrator can reconcile the discrepancy or the IFDA 10 or the log of the chambers 40, 40', 40" is otherwise reset.

Figures 5, 6:
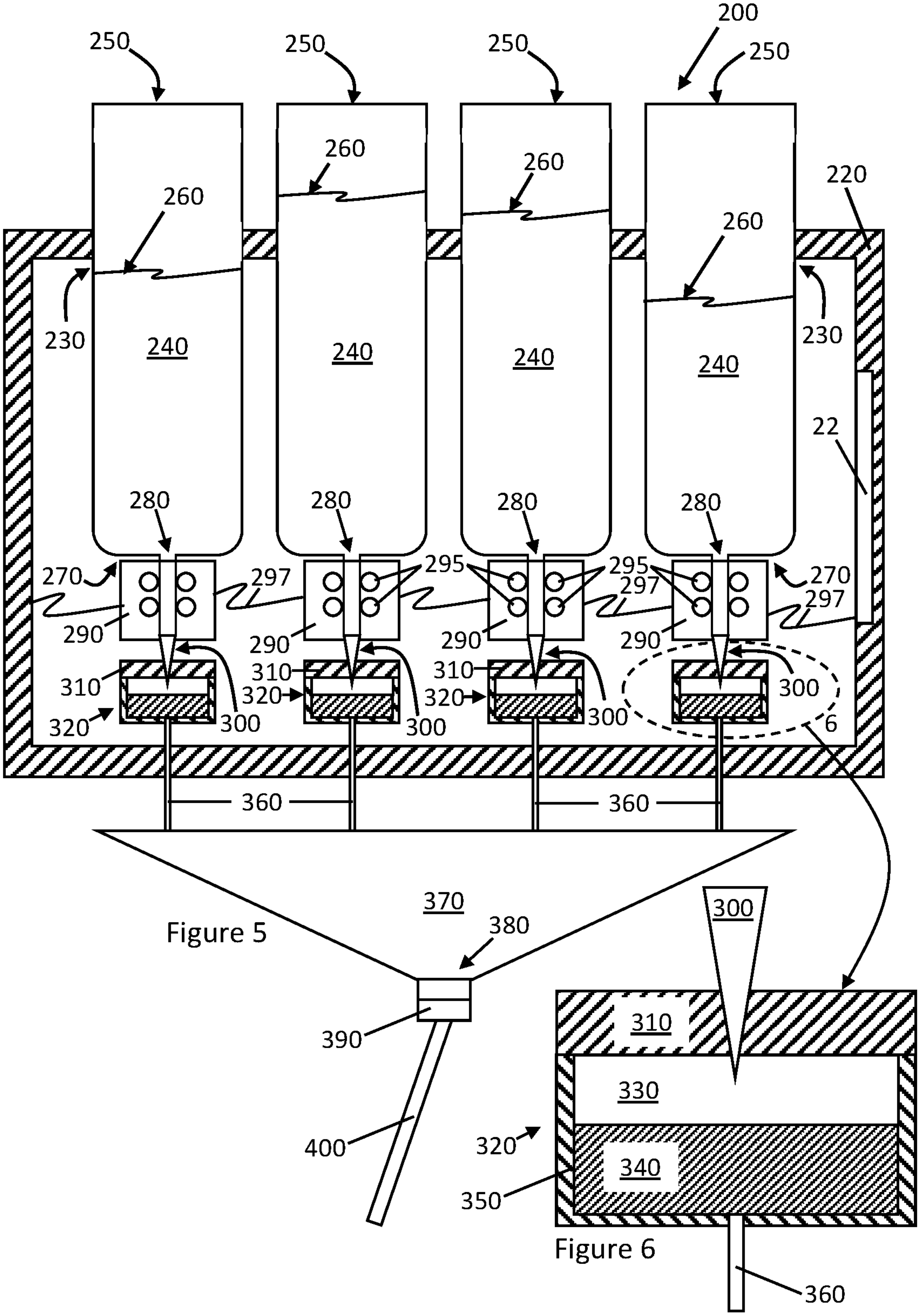
FIG. 5 is a schematic view of an exemplary second embodiment of an intravenous fluid delivery apparatus.
FIG. 6 is an enlarged view of the disposable and replaceable distribution component of the exemplary second embodiment of an intravenous fluid delivery apparatus illustrated in FIG. 5.

Referring to FIG. 5, another embodiment of an intravenous fluid delivery apparatus (IFDA) 200 is illustrated in schematic cross-section as having a body 220 having a plurality of openings or docks 230. Each opening or dock 230 accommodates and/or engages with a bottle or container 240, for example without limitation an elongate cylindrical bottle as illustrated in FIG. 5. Four openings or docks 230 are illustrated in FIG. 5; however, the actual number of openings or docks 230 may be for example without limitation, 1, 2, 3, 4, 5, 6 or more. In one embodiment each bottle 240 includes an open top end 250, and each bottle 240 accommodates and/or engages with a collapsible bag 260 containing a fluid. Other embodiments include a bottle 240 having a solid top end 250 without the collapsible bag 260 disposed within. The bottles 240 may extend above a top of the body 220 as illustrated in FIG. 5 or may be positioned such that an entirety of each bottle 240 is disposed within the body 220.

Disposed near a bottom end 270 of each bottle 240 a tubular extending portion 280 is disposed through an electronic interface unit (EIU) 290. For those embodiments including a collapsible bag 260, the tubular extending portion 280 is part of the collapsible bag 260. However, for those embodiments lacking a collapsible bag 260, the tubular extending portion 280 is just an extension of each bottle 240.

Similar to the chambers 40, 40', 40", an identification code or identifying element is printed on or otherwise electronically applied to each bottle 240 or collapsible bag 260, for example on the tubular extending portion 280. For example, without limitation, the identification code or identifying element may be in the form of a barcode, a VR code, a decimal or alphanumeric code, an RFID tag, or any sort of identification device whether electronic or optical or both as may be known in the art. The identification code or identifying element uniquely identifies each bottle 240 or each collapsible bag 260 by corresponding to a matching identification code stored for data regarding the contents of each bottle 240 or each collapsible bag 260, where the data is stored in a database or lookup table, or the like as is known in the art.

Like the embodiments described hereinabove, the same structures and techniques employed to prevent diversion of fluid from within the chambers 40, 40', 40" are also applicable to the bottles 240 or the collapsible bags 260. In any of the embodiments disclosed herein, power required for erasing a flash memory or otherwise erasing or overwriting a non-permanent memory on any of the chambers 40, 40', 40" or the bottles 240 or the collapsible bags 260 is provided by a capacitor or a storage cell or any power storage element as is known in the art that is disposed in or on the chamber 40, 40', 40", the bottle 240, or the bag 260 and that may be charged via a solar element or via direct charging from a connection with the IFDA 10, 200 or from an external charger through a charging port as is known in the art.

The EIU 290 includes circuitry that communicates electronically with a computing system, for example the user interface 110 described hereinabove, having access to the database or lookup table or the like. The electronic communication may be through a wired connection, for example as illustrated by the wires 297 connecting between the EIUs 290 and the body 220 in FIG. 5, or may be via a wireless connection, for example without limitation, a Bluetooth connection, a WiFi connection, or any other wired or wireless electronic communication connection as is known in the art.

When a bottle 240 or a collapsible bag 260 is positioned with the tubular extending portion 280 extending through the EIU 290, a reader in the EIU 290, for example without limitation, a barcode reader, an optical scanner, an RFID tag reader, or any sort of reader device whether electronic or optical or both as may be known in the art reads the identification code on the tubular extending portion 280, and matches the identification code to the corresponding identification code for data regarding the contents of the bottle 240 or the collapsible bag 260 in the database or lookup table or the like. The data regarding the contents of each bottle 240 or collapsible bag 260 stored in the database includes at least the particular fluid, the concentration of the fluid, and the volume of the fluid within the bottle 240 or the collapsible bag 260. When the reader in the EIU 290 has matched the identification code read from the tubular extending portion 280 to the corresponding identification code for data in the database, the data is communicated to the user interface 110. If, however, the reader in the EIU 290 cannot match the identification code read from the tubular extending portion 280 to an identification code in the database, then the contents of the bottle 240 or collapsible bag 260 remain unverified, and the bottle 240 or collapsible bag 260 is rejected for use in the IFDA 200.

Still referring to FIG. 5, in one embodiment a needle 300 extends from the tubular extending portion 280. Those embodiments including a collapsible bag 260 have the needle 300 extending from the tubular extending portion 280 of the collapsible bag 260. Those embodiments lacking a collapsible bag 260 have the needle 300 extending from the tubular extending portion 280 of the bottle 240. The needle

300 has a lumen through which the fluid within the collapsible bag 260 or the bottle 240 may flow.

Referring now to FIGS. 5 and 6, when the tubular extending portion 280 is disposed through the EIU 290 as illustrated in FIG. 5, the needle 300 is positioned to pierce through a membrane 310 that forms a top surface of a disposable and replaceable distribution component 320. For example, in one embodiment the membrane 310 is a rubber membrane. In other embodiments the membrane 310 could be any natural or synthetic material suitable for piercing by the needle 300 and forming a seal around the needle 300 as is known in the art. One of the disposable and replaceable distribution elements 320 as denoted by the dashed circle 6 in FIG. 5 is illustrated enlarged in FIG. 6

Referring to FIG. 6, a sharp tip of the needle 300 penetrates through the membrane 310 into a space 330 above a filter 340 that is disposed within a housing 350 of the disposable and replaceable distribution element 320. A fluid flows through the tubular extending portion 280, through the lumen of the needle 300 and into the space 330 where it drops onto the filter 340. The physical separation provided by the space 330 between a tip of the needle 300 and the filter 340 also serves as a separation between a sterile side and a patient side of the IFDA 200. Each of the disposable and replaceable distribution components 320 can be replaced after every patient to further ensure a separation between the sterile side and the patient side of the IFDA 200.

Referring back to FIG. 5, in one embodiment each of the EIUs 290 further includes two or more opposed rollers 295 or other mechanism as is known in the art for squeezing or pushing the fluid through the tubular extending portion 280 and into the disposable and replaceable distribution element 320. For example, in one embodiment the two or more rollers 295 are each journaled on an independent axle that can be moved up and down and laterally relative to the tubular extending portion 280 so that when moved together in a coordinated motion the rollers 295 compress the tubular extending portion 280 while applying a downward force to the contents of the tubular extending portion 280. The two or more rollers 295 are controlled by the circuitry within each EIU 290, for example without limitation, via actuators, gears, and other mechanisms as are known in the art.

Each EIU 290 also includes a flow metering and/or flow measurement capability (not shown), so that, for example, in one embodiment the volume of the fluid passing out of a bottle 240 or collapsible bag 260 and through each EIU is metered by precise control of the two or more rollers 295 as defined hereinabove. Such systems having rollers and a metering mechanism are known in the art in the context of IV pumps that are currently available. While the flow metering mechanism within each EIU 290 is capable of operating for long term infusions like currently available IV pumps, the flow metering mechanism with each EIU 290 is primarily intended for intra-operative bolus delivery of the fluids. In another embodiment, each EIU has a flow meter (not shown) instead of or in addition to each of the flow metering mechanisms whereby the flow of fluid through each EIU 290 is measured.

Whether metered by precise control of the two or more rollers 295, or measured by a flow meter (not shown), or both metered and measured, the volume of fluid passing out of each bottle 240 or collapsible bag 260 and through each EIU 290 is recorded in the database in association with the data regarding the contents of each bottle 240 or collapsible bag 260. In this way the volume of the contents of every bottle 240 or collapsible bag 260 can be tracked and safe guarded against improper or unauthorized use.

A tube or pipe 360, for example without limitation, a microbore tubing 360 extends from each of the disposable and replaceable distribution elements 320 and provides fluid connection between an interior volume of each disposable and replaceable distribution element 320 and an interface or manifold 370. In one embodiment, each of the plurality of tubes 360 is individually disposed through the body 220 as illustrated in FIG. 5. However, in other embodiments the plurality of tubes 360 is gathered together into a bundle before being passed through the body 220. In some embodiments, like the disposable and replaceable distribution components 320 described hereinabove, both the plurality of tubes 360 and the manifold 370 are disposable and in use are replaced after every patient.

Referring to FIG. 5, three disposable elements can be seen to be serially arranged below each EIU 290. In particular, a disposable and replaceable distribution component 320 is connected below each EIU 290 by a tube 360 to the manifold 370. In some embodiments, the three disposable elements can be built into one or more detachably attachable cartridges. For example without limitation in some embodiments the manifold 370 snaps into an opening (not shown) in the body 220 thereby closing the opening while being connected with the disposable and replaceable distribution components 320 via the tubes 360. In these embodiments the manifold 370 snaps out of the opening and the tubing 360 and disposable and replaceable distribution components 320 are easily accessible for removal through the opening. In other embodiments, for example without limitation, the manifold 370 snaps into an opening (not shown) in the body 220 and is integrally connected to the disposable and replaceable distribution components 320 via the tubes 360. In these embodiments all three of the disposable elements (320, 360, 370) snap out of the opening for disposal and replacement.

The manifold 370 fluidly connects the plurality of tubes 360 to an output 380 of the manifold 370. A connector or fitting 390, for example without limitation a luer lock connector 390 or other connector for tubing as is known in the art is provided at the output 380 of the manifold 370. The connector 390 connects the output 380 of the manifold 370 to a patient intravenous (IV) line 400. The manifold 370 therefore combines all of the fluids from each of the bottles 240 before delivery of the combined fluids to a patient IV line 400.

The IFDA 200 includes a computing system or user interface, hereinafter referred to as the second embodiment of the user interface, that includes all of the structure and functionality of the user interface 110 described hereinabove and illustrated in FIG. 1. For example without limitation, in one embodiment the second embodiment of the user interface includes a touchscreen tablet built into a panel of the body 220. The second embodiment of the user interface communicates with each of the EIUs 290 allowing a user to enter a predetermined amount, for example a predetermined volume, of each fluid to be dispensed by each EIU 290. As noted hereinabove, the amount of each fluid delivered is tracked and stored in the database for each bottle 240 and or collapsible bag 260 for reconciliation of the use of the fluids.

INDUSTRIAL APPLICABILITY

An apparatus for administration of fluids is presented in multiple embodiments. One embodiment includes fluid specific docks into which only chambers containing the specific fluids can be inserted and from which the chambers cannot be removed without entry of a passcode. Another embodiment includes bottles or collapsible bags having identifying codes on them that are read by electronic control devices that pump the fluid out of the bottles or collapsible bags. Predetermined volumes of the fluids can precisely and safely be administered by either embodiment, while the usage of all of the fluids can be tracked and controlled. The IFDA can be manufactured by industry for use by medical professionals.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

I claim:

1. A container, comprising:

a container identifying element that is unique to the container, wherein the container identifying element is adapted to correspond to a matching database identification code that is associated with data stored in a database, wherein the data comprises a type and quantity of fluid within the container, wherein the container identifying element is selected from the group consisting of a barcode, a VR code, a decimal code, an alphanumeric code, an RFID tag, and a combination thereof;

a tamper resistant mechanism disposed on the container, wherein the tamper resistant mechanism comprises a non-permanent memory connected to an electronic circuit, wherein a passcode is stored in the non-permanent memory;

a container body, the electronic circuit located on the container body;

a closure member selected from the group consisting of a cap, a cover over an opening, and a valve disposed on the container body, the closure member configured to open or close the container to selectively gain access to the fluid therein;

an electrical connection comprising an electrical pathway extending between the electronic circuit located on the container body and an electrical contact located on the closure member, wherein the electrical pathway is located to interrupt the electrical connection between the electronic circuit located on the container body and the electrical contract located on the closure member in response to actuating the closure member to open the container, wherein breaking the electrical connection causes the electronic circuit to erase the non-permanent memory; and a locking mechanism adapted to lock the container within a fluid delivery device having circuitry and a user interface, wherein the locking mechanism is disabled by entry of the passcode into the user interface, wherein the non-permanent memory is located to be read by said circuitry of the fluid delivery device upon insertion of the container therein, and wherein said erasure of the passcode from the non-permanent memory in response to opening the container and breaking the electrical connection causes the fluid delivery device to reject the container as lacking the passcode.

2. The container of claim 1, further comprising a set of splines or pins extending therefrom, wherein the set of splines or pins is indicative of the type of fluid disposed within the container.

3. The container of claim 1, further comprising an extending portion that extends from an end of the container, wherein the extending portion further comprises a needle that extends from an end of the extending portion.

4. A container, comprising a tamper resistant mechanism disposed on the container, wherein the tamper resistant mechanism comprises a non-permanent memory connected to an electronic circuit, wherein a passcode is stored in the non-permanent memory;

a container body, the electronic circuit located on the container body;

a closure member selected from the group consisting of a cap, a cover over an opening, and a valve disposed on the container body, the closure member configured to open or close the container to selectively gain access to the fluid therein; and an electrical connection comprising an electrical pathway extending between the electronic circuit located on the container body and an electrical contact located on the closure member, wherein the electrical pathway is located to interrupt the electrical connection between the electronic circuit located on the container body and the electrical contract located on the closure member in response to actuating the closure member to open the container, wherein breaking the electrical connection causes the electronic circuit to erase the non-permanent memory; and a locking mechanism adapted to lock the container within a fluid delivery device having circuitry and a user interface, wherein the locking mechanism is disabled by entry of the passcode into the user interface, wherein the non-permanent memory is located to be read by said circuitry of the fluid delivery device upon insertion of the container therein, and wherein said erasure of the passcode from the non-permanent memory in response to opening the container and breaking the electrical connection causes the fluid delivery device to reject the container as lacking the passcode.

5. The container of claim 4, further comprising a power storage element.

6. The container of claim 4, further comprising:

a container identifying element that is unique to the container, wherein the container identifying element is adapted to correspond to a matching database identification code that is associated with data stored in a database, wherein the data comprises a type and quantity of fluid within the container.

7. The container of claim 6, wherein the container identifying element is selected from the group consisting of a barcode, a VR code, a decimal code, an alphanumeric code, an RFID tag, and a combination thereof.

8. The container of claim 4, further comprising a set of splines or pins extending therefrom, wherein the set of splines or pins is indicative of a type of fluid disposed within the container.

9. The container of claim 4, further comprising an extending portion that extends from an end of the container, wherein the extending portion further comprises a needle that extends from an end of the extending portion.

10. A container, comprising:

a container identifying element that is unique to the container, wherein the container identifying element is adapted to correspond to a matching database identification code that is associated with data stored in a database, wherein the data comprises the type and quantity of fluid within the container; and a tamper resistant mechanism disposed on the container, wherein the tamper resistant mechanism comprises a non-permanent memory connected to an electronic circuit, wherein a passcode is stored in the non-permanent memory;

a container body, the electronic circuit located on the container body;

a closure member selected from the group consisting of a cap, a cover over an opening, and a valve disposed on the container body, the closure member configured to open or close the container to selectively gain access to the fluid therein; and an electrical connection comprising an electrical pathway extending between the electronic circuit located on the container body and an electrical contact located on the closure member, wherein the electrical pathway is located to interrupt the electrical connection between the electronic circuit located on the container body and the electrical contract located on the closure member in response to actuating the closure member to open the container, wherein breaking the electrical connection causes the electronic circuit to erase the non-permanent memory; and a locking mechanism adapted to lock the container within a fluid delivery device having circuitry and a user interface, wherein the locking mechanism is disabled by entry of the passcode into the user interface, wherein the non-permanent memory is located to be read by said circuitry of the fluid delivery device upon insertion of the container therein, and wherein said erasure of the passcode from the non-permanent memory in response to opening the container and breaking the electrical connection causes the fluid delivery device to reject the container as lacking the passcode.

11. The container of claim 10, wherein the container identifying element is selected from the group consisting of a barcode, a VR code, a decimal code, an alphanumeric code, an RFID tag, and a combination thereof.

12. The container of claim 10, further comprising a set of splines or pins extending therefrom, wherein the set of splines or pins is indicative of the type of fluid disposed within the container.

* * * * *